US011298083B2

United States Patent
Dawoud et al.

(10) Patent No.: US 11,298,083 B2
(45) Date of Patent: Apr. 12, 2022

(54) METHODS AND SYSTEMS FOR DETECTING LOSS OF ELECTRODE-TISSUE CONTACT

(71) Applicant: Pacesetter, Inc, Sylmar, CA (US)

(72) Inventors: Fady Dawoud, Studio City, CA (US); Alan B. Vogel, Santa Clarita, CA (US); Kurt Salek, Santa Clarita, CA (US)

(73) Assignee: PACESETTER, INC., Sylmar, CA (US)

( * ) Notice: Subject to any disclaimer, the term of this patent is extended or adjusted under 35 U.S.C. 154(b) by 303 days.

(21) Appl. No.: 16/572,144

(22) Filed: Sep. 16, 2019

(65) Prior Publication Data
US 2021/0077028 A1     Mar. 18, 2021

(51) Int. Cl.
*A61B 5/06* (2006.01)
*A61B 5/00* (2006.01)

(52) U.S. Cl.
CPC .......... *A61B 5/6886* (2013.01); *A61B 5/068* (2013.01); *A61B 5/686* (2013.01); *A61B 5/7225* (2013.01)

(58) Field of Classification Search
CPC ....... A61B 5/352; A61B 5/366; A61B 5/7203; A61B 5/7225; A61N 1/3756
See application file for complete search history.

(56) References Cited

U.S. PATENT DOCUMENTS

2019/0336026 A1*  11/2019  Dawoud ............ A61B 5/366

* cited by examiner

*Primary Examiner* — Jon C Morales
(74) *Attorney, Agent, or Firm* — The Small Patent Law Group LLC; Dean D. Small (57) ABSTRACT

An implantable cardiac monitor (ICM) and a computer implemented method are provided. The ICM includes electrodes that are configured to sense analog cardiac activity (CA) signals when engaged with tissue at a location remote from the heart. One or more of the electrodes transition between an engaged state and disengaged state with respect to the tissue. An analog to digital (A/D) converter communicates with the electrodes along a data signal path. The A/D converts the analog CA signals to digital CA signal. An electrode-tissue feedback (ETF) circuit is provided along the data signal path between the electrodes and the A/D converter. The ETF circuit generates a feedback signal component into the data signal path when one or more of the electrodes is in the disengaged state. The feedback signal component is superimposed onto the analog CA signals. One or more processors executes program instructions in connection with collecting and analyzing the digital CA signals when the one or more electrodes are in the engaged state.

20 Claims, 6 Drawing Sheets

METHODS AND SYSTEMS FOR DETECTING LOSS OF ELECTRODE-TISSUE CONTACT

BACKGROUND

Embodiments herein generally relate to methods and systems for detecting loss of electrode-tissue contact for cardiac monitors.

Implantable cardiac monitors (ICMs) are devices that may be implanted under a patient's skin to continuously monitor the patient's cardiac activity. An ICM may be programmed to detect and record cardiac information and episodes such as atrial/ventricular tachycardia, atrial fibrillation, bradycardia, asystole, and the like. Triggers for detecting and recording an event (e.g., such a tachy/brady detection rate, a number of events, and/or a duration of asystole) may be programmed by a clinician. Alternatively, when the patient experiences symptoms, the patient may activate the detection and recording using an external patient activator. Diagnostics and recorded events may be downloaded by a local external device, by the clinician in-clinic using a programmer, and in other manners.

ICMs allow clinicians to monitor the patient's cardiac activity for an extended period of time. The information recorded by ICMs enables clinicians to determine if a patient has irregularities in their heart rhythm that cannot be confirmed in the clinic, particularly for transient and/or infrequent arrhythmias. The information can also aid the clinician in determining the best course of treatment for the patient (e.g., an addition or change of medication, a procedure such as cardioversion or ablation to restore a regular heart rhythm, and/or implantation of a pacemaker or implantable cardioverter defibrillator for long-term treatment of an irregular heart rhythm).

In some configurations, the ICM senses physiologic signals, such as cardiac signals associated with a series of cardiac beats, through a combination of electrodes provided on a housing of the ICM. The electrodes are remote from the heart and are configured to engage the patient's tissue in a subcutaneous pocket where the ICM is implanted. As a patient moves, the ICM may shift within the pocket which creates a potential for the electrodes to separate or disengage from the surrounding tissue. When the electrodes become disengaged, the electrodes no longer correctly sense physiologic signals. It is important to maintain adequate electrode-tissue contact in order to accurately sense cardiac signals. Loss of adequate electrode-tissue contact can occur in various degrees due to factors such as implantation technique, physician experience, patient postural changes, electrode surface area, subcutaneous tissue variation, and the like. Loss of adequate electrode-tissue contact may lead to the occurrence of false triggers which appear on recorded cardiac signals as long episodes of complete lack of cardiac activity (e.g., an asystole and/or pause) resembling a fatal complete third-degree heart block. These false triggers lead to physician and clinic confusion and uncertainty in acting to contact the patient. Accordingly, a desire remains to improve the reliability of cardiac signal detection and analysis to eliminate false triggers resulting from loss of adequate electrode-tissue contact.

SUMMARY

In accordance with embodiments herein, an implantable cardiac monitor (ICM) is provided. The ICM includes electrodes that are configured to sense analog cardiac activity (CA) signals when engaged with tissue at a location remote from the heart. One or more of the electrodes transition between an engaged state and disengaged state with respect to the tissue. An analog to digital (A/D) converter communicates with the electrodes along a data signal path. The A/D converter is configured to convert the analog CA signals to digital CA signal. An electrode-tissue feedback (ETF) circuit is provided along the data signal path between the electrodes and the A/D converter. The ETF circuit is configured to generate a feedback signal component into the data signal path when one or more of the electrodes is in the disengaged state. The feedback signal component is superimposed onto the analog CA signals. One or more processors are configured to execute program instructions in connection with collecting and analyzing the digital CA signals when the one or more electrodes are in the engaged state.

Optionally, the ICM may include an amplifier circuit connected to the electrodes along the data signal path and may be configured to amplify the analog CA signals. The ETF circuit interacts with the amplifier circuit to introduce the feedback signal component into the data signal path. A voltage reference signal path may be configured to provide a reference voltage. The ETF circuit may be configured to generate the feedback signal component into the voltage reference signal path such that the feedback signal component is superimposed onto the analog CA signals. The ETF circuit may be configured to detect a loss of electrode-tissue contact (LOC) condition corresponding to the disengaged state, and based thereon, the ETF circuit may be configured to introduce the feedback signal component. The ETF circuit may detect the LOC condition based on an input impedance at the electrodes. The ETF circuit may generate the feedback signal component in response to an input impedance at the electrodes exceeding a predetermined impedance threshold.

Optionally, the feedback signal component may oscillate at a first frequency within a first predetermined frequency range that may be greater than frequencies associated with physiologic characteristics of interest sensed by the electrodes in the analog CA signals. The A/D converter may convert the feedback signal component, through downsampling, to an aliased second frequency within a second predetermined frequency range. The one or more processors may identify a loss of electrode-tissue contact (LOC) condition when the feedback signal component is present within the digital CA signals at the aliased second frequency. The ETF circuit may be configured to generate the feedback signal component at a first amplitude based on an input impedance at the electrodes exceeding a predetermined impedance threshold. The one or more processors may identify a loss of electrode-tissue contact (LOC) condition when the feedback signal component having the first amplitude is present within the digital CA signals.

Optionally, the ETF circuit may be configured to generate the feedback signal component at a first frequency based on an input impedance at the electrodes exceeding a predetermined impedance threshold. The one or more processors may identify a loss of electrode-tissue contact (LOC) condition when the feedback signal component having the first frequency is present within the digital CA signals. The ETF circuit may be configured to generate the feedback signal component with a non-physiologic shape based on an input impedance at the electrodes exceeding a predetermined impedance threshold. The one or more processors may identify a loss of electrode-tissue contact (LOC) condition when the feedback signal component having the non-physiologic shape is present within the digital CA signals. The ICM may include a housing enclosing the A/D converter, ETF circuit and one or more processors. The electrodes may be provided on the housing. The housing may be implanted in a subcutaneous pocket. The electrodes may be configured to engage within the subcutaneous pocket in connection with remotely monitoring heart activity.

In accordance with embodiments herein, a computer implemented method for detecting a loss of electrode-tissue contact (LOC) condition for an implantable cardiac monitor (ICM) is provided. The method configures electrodes to sense analog cardiac activity (CA) signals when engaged with tissue at a location remote from the heart. One or more of the electrodes transition between an engaged state and disengaged state with respect to the tissue. The method detects when one or more of the electrodes is in the disengaged state. The method generates a feedback signal component when the one or more of the electrodes is in the disengaged state. The method superimposes the feedback signal component onto the analog CA signals and converts the analog CA signals to digital CA signals. The digital CA signals include the feedback signal component. The method analyzes the digital CA signals for a presence of the feedback signal component in connection with determining whether one or more of the electrodes is in the engaged or disengaged state and collects and analyzing the digital CA signals when the one or more electrodes are in the engaged state.

Optionally, the method may amplify the analog CA signals. The superimposing may comprise introducing a feedback signal component into the data signal path using an electrode-tissue feedback (ETF) circuit. The generating may further comprise generating the feedback signal component into a voltage reference signal path such that the feedback signal component is superimposed onto the analog CA signals. The detecting may further comprise detecting the LOC condition based on an input impedance at the electrodes. The converting may further comprise converting the feedback signal, through downsampling, to an aliased second frequency within a second predetermined frequency range. The analyzing may further comprise identifying an LOC condition when the feedback signal component is present within the digital CA signals at the aliased second frequency.

Optionally, the generating may further comprise generating the feedback signal component at a first amplitude based on an input impedance at the electrodes exceeding a predetermined impedance threshold. The analyzing may further comprise identifying an LOC condition when the feedback signal component having the first amplitude is present within the digital CA signals. The generating may further comprise generating the feedback signal component at a first frequency based on an input impedance at the electrodes exceeding a predetermined impedance threshold. The analyzing may further comprise identifying an LOC condition when the feedback signal component having the first frequency is present within the digital CA signals. The generating may further comprise generating the feedback signal component with a non-physiologic shape based on an input impedance at the electrodes exceeding a predetermined impedance threshold. The analyzing may further comprise identifying an LOC condition when the feedback signal component having the non-physiologic shape is present within the digital CA signals.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Terms

The terms "engaged state" and "attached state" shall mean a condition in which one or more electrodes of the ICM contact and are conductively seated against the underlying tissue to a degree that maintains an input impedance below a predetermined threshold value. It is recognized that, when in an engaged state, the surface areas of the one or more electrodes in the ICM may be entirely in contact with the underlying tissue. For example, in an engaged state, the surface areas of both a first electrode and a second electrode may be entirely in contact with the underlying tissue. Additionally, when in an engaged state, a small portion of the surface areas of the one or more electrodes in the ICM may not contact the underlying tissue (e.g., less than 25% of the surface area of one or more electrodes in the ICM).

The terms "disengaged state" and "detached state" shall mean a condition in which one or more of the electrodes are at least partially disconnected in a non-conductive arrangement with the underlying tissue to a degree that maintains an input impedance at or above a predetermined threshold value. In the disengaged state, one or more of the electrodes of the ICM may be entirely, or only partly, separated from the underlying tissue, where the extent of separation is sufficient to give rise to an input impedance at the one or more electrodes that is at or above the predetermined threshold value. By way of example, the one or more electrodes of the ICM may be considered to be in a disengaged state when more than 25% of the surface area of one or more electrodes in the ICM are not properly seated against the underlying tissue. As another example, one or more electrodes of the ICM may be considered to be in a disengaged state, independent of the surface area of the electrodes seated against the underlying tissue, but instead based on the input impedance at the one or more electrodes exceeding the predetermined threshold value. For example, when the nature of the engagement between the one or more electrodes of the ICM results in an input impedance that exceeds the predetermined threshold value, the one or more electrodes of the ICM may be considered to be in a disengaged state. For example, a nature of the engagement that gives rise to an input impedance above the predetermined threshold value may be when the ICM moves or shifts causing intermittent engagement of the one or more electrodes with the underlaying tissue. As another example, a nature of the engagement that gives rise to an input impedance that exceeds the predetermined threshold value may be when one or more of the electrodes of the ICM are not firmly pressed against the tissue.

System Overview

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method and System to Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device" and U.S. Pat. No. 9,232,485 "System and Method For Selectively Communicating With An Implantable Medical Device", which are hereby incorporated by reference. Additionally or alternatively, the IMD may include one or more structural and/or functional aspects of the device(s) described in U.S. patent application Ser. No. 15/973,126, titled "Method And System For Second Pass Confirmation Of Detected Cardiac Arrhythmic Patterns", U.S. patent application Ser. No. 15/973,351, titled "Method And System To Detect R-Waves In Cardiac Arrhythmic Patterns", U.S. patent application Ser. No. 15/973,307, titled "Method And System To Detect Post Ventricular Contractions In Cardiac Arrhythmic Patterns", and U.S. patent application Ser. No. 16/399,813, titled "Method And System To Detect Noise In Cardiac Arrhythmic Patterns", which are each hereby incorporated by reference.

Additionally or alternatively, the IMD may include one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties.

Further, one or more combinations of IMDs may be utilized from the above incorporated patents and applications in accordance with embodiments herein.

The methods and systems described herein may employ all or portions of structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, where indicated, the methods may be fully or partially implemented by one or more processors of one or more devices or systems. While the operations of some methods may be described as performed by the processor(s) of one device, additionally, some or all of such operations may be performed by the processor(s) of another device described herein.

Figure 1:
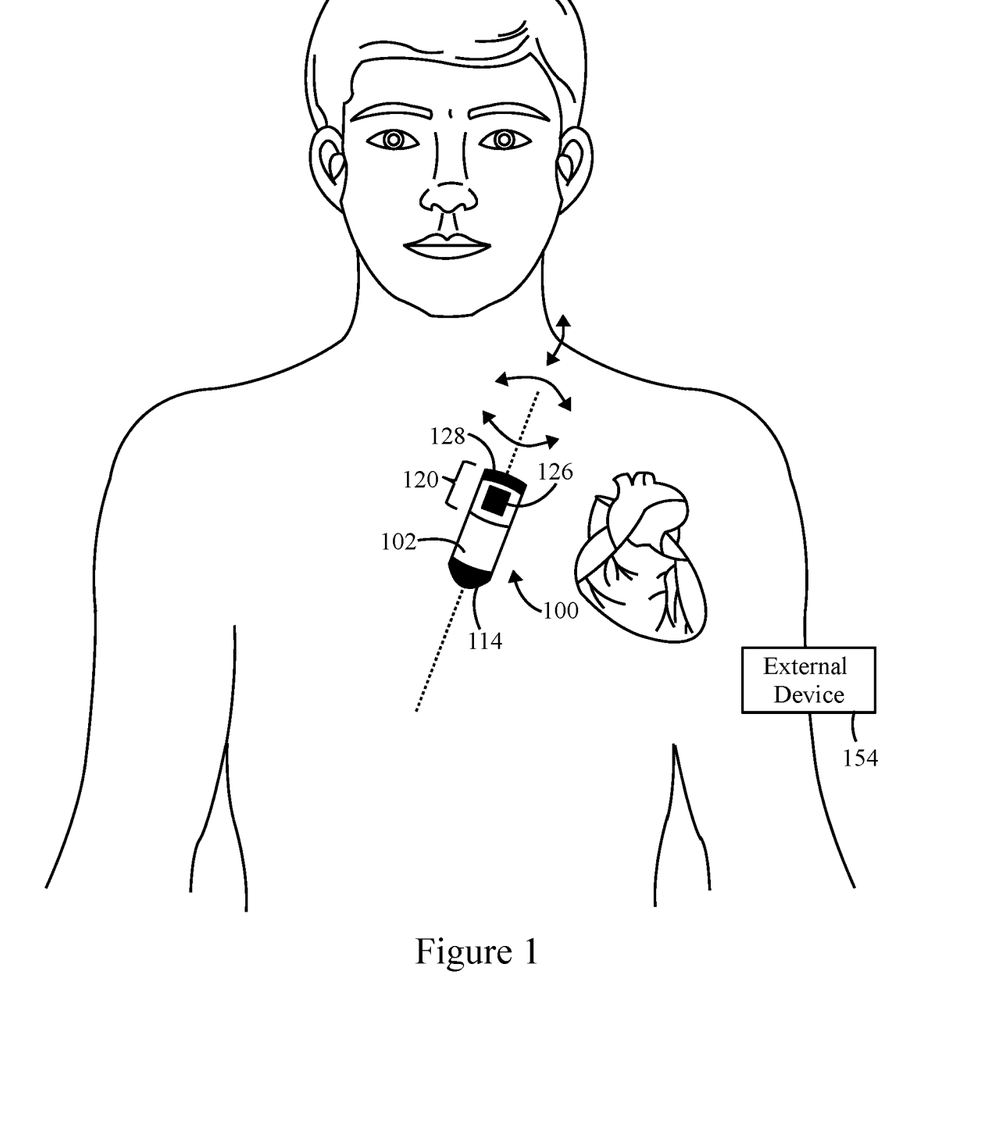
FIG. 1 illustrates an implantable cardiac monitoring device (ICM) intended for subcutaneous implantation at a site near the heart in accordance with embodiments herein.

FIG. 1 illustrates an example ICM 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of cardiac activity (CA) data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sense electrodes 114, 126 may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias, pauses, Brady episodes and the like and if a pause, Brady episode, arrhythmia, and the like is detected, automatically records the CA signals in memory for subsequent transmission to an external device or external instrument (EI) 154. The CA signal processing and detection is provided for, at least in part, by algorithms embodied in or implemented by one or more microprocessors in the ICM 100. The ICM 100 includes one or more processors and memory that stores program instructions directing the processors to implement arrhythmia, including atrial fibrillation (AF), pause, bradycardia episode, and the like detection utilizing an onboard R-R interval irregularity (ORI) process that analyzes cardiac activity signals collected over one or more sensing channels.

As explained herein, the ICM 100 includes electrodes 114, 126 that collect CA signals in connection with multiple cardiac beats when engaged with tissue at a location remote from the heart. The electrodes 114, 126 of the ICM may transition between an engaged state and a disengaged state with respect to the tissue based on the degree of electrode-tissue contact. Loss of adequate electrode-tissue contact resulting in a disengaged state may occur due to factors such as implantation technique, physician experience, patient postural changes, electrode surface area, subcutaneous tissue variation, and the like. ICM electrodes in a disengaged state may lead to the occurrence of false triggers which appear on recorded cardiac signals as long episodes of complete lack of cardiac activity (e.g., an asystole and/or pause) resembling a fatal complete third-degree heart block. False triggers due to electrodes in a disengaged state lead to physician and clinic confusion and uncertainty in acting to contact the patient.

The ICM 100 includes an electrode-tissue feedback (ETF) circuit that is configured to detect a loss of electrode-tissue contact (LOC) condition corresponding to a disengaged state of the one or more electrodes. The ETF circuit is positioned between the one or more electrodes and an analog to digital (A/D) converter of the ICM 100. The ETF circuit detects the LOC condition based on an input impedance at the one or more electrodes. The ICM 100 converts the analog CA signals collected by the one or more electrodes to digital CA signals at the A/D converter. The processors of the ICM 100 execute program instructions in connection with collecting and analyzing the digital CA signals. When the one or more electrodes are in a disengaged state, the ETF detects the LOC condition and generates a feedback signal component. The feedback signal component is superimposed onto the analog CA signals. The processors of the ICM 100 identify the LOC condition when the feedback signal component is present within the digital CA signals and, based thereon, execute program instructions in connection with avoiding a false trigger event as described further below.

Figure 2:
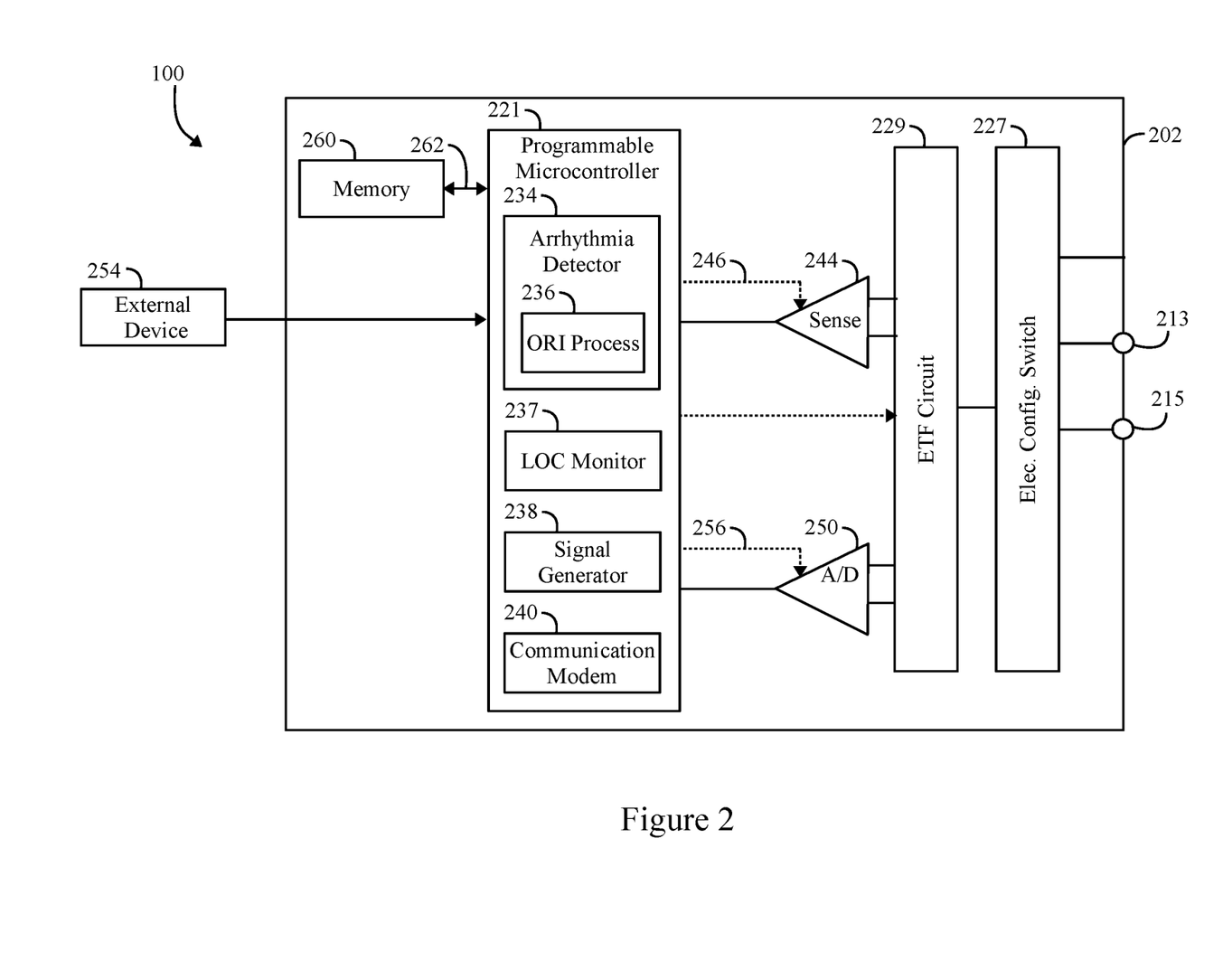
FIG. 2 illustrates a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 202 to hold the electronic/computing components. The housing 202 (which is often referred to as the "can," "case," "encasing," or "case electrode") may be programmably selected to act as an electrode for certain sensing modes. Housing 202 further includes a connector (not shown) with at least one terminal 213 and optionally additional terminals 215. The terminals 213, 215 may be coupled to sensing electrodes that are provided upon or immediately adjacent the housing 202. Optionally, more than two terminals 213, 215 may be provided in order to support more than two sensing electrodes, such as for a bipolar sensing scheme that uses the housing 202 as a reference electrode. Additionally or alternatively, the terminals 213, 215 may be connected to one or more leads having one or more electrodes provided thereon, where the electrodes are located in various locations about the heart. The type and location of the electrodes may vary.

The ICM 100 includes a programmable microcontroller 221 that controls various operations of the ICM 100, including cardiac monitoring. Microcontroller 221 includes a microprocessor (or equivalent control circuitry), RAM and/or ROM memory, logic and timing circuitry, state machine circuitry, and I/O circuitry. The microcontroller 221 also performs the operations described herein in connection with collecting cardiac activity data and analyzing the cardiac activity data to, among other things, detect a LOC condition of the one or more electrodes.

A switch 227 is optionally provided to allow selection of different electrode configurations under the control of the microcontroller 221. The electrode configuration switch 227 may include multiple switches for connecting the desired electrodes to the appropriate I/O circuits, thereby facilitating electrode programmability. The switch 227 is controlled by a control signal from the microcontroller 221. Optionally, the switch 227 may be omitted and the I/O circuits directly connected to the housing electrode 114 and a second electrode 126.

The ICM 100 includes an ETF circuit 229 provided along the data signal path between the one or more electrodes and the A/D converter of a A/D data acquisition system (DAS) 250. In one example, the ETF circuit 229 may be implemented along the data signal path between the switch 227 and the A/D converter of the DAS 250. Optionally, the ETF circuit 229 may also be positioned between the switch 227 and the sensing circuit 244. The ETF circuit 229 is configured to generate a feedback signal component into the data signal path when one or more of the electrodes is in the disengaged state. The ETF circuit 229 detects a loss of contact (LOC) condition corresponding to the disengaged state of the one or more electrodes based on an input impedance at the one or more electrodes exceeding a predetermined threshold value. The ETF circuit 229 generates the feedback signal component in response to the LOC condition.

Microcontroller 221 includes an arrhythmia detector 234 that is configured to analyze cardiac activity signals to identify potential AF episodes as well as other arrhythmias (e.g., Tachycardias, Bradycardias, Asystole, etc.), and a signal generator 238 for generating signals based on CA, LOC conditions, and the like. By way of example, the arrhythmia detector 234 may implement an AF detection algorithm as described in U.S. Pat. No. 8,135,456, the complete subject matter of which is incorporated herein by reference. Although not shown, the microcontroller 221 may further include other dedicated circuitry and/or firmware/software components that assist in monitoring various conditions of the patient's heart and managing pacing therapies.

Microcontroller 221 also includes an LOC monitor 237 that analyzes the CA signals for the feedback signal component indicative of an LOC condition. When the feedback signal component is present, the microcontroller 221 executes program instructions to stop recording and analyzing the CA signals until the LOC condition is no longer present for a select time period. If the microcontroller 221 stops recording the CA signals, the microcontroller 221 continues to monitor the CA signals for the feedback signal component and reinitiates recording and analyzing the CA signals when the feedback signal component is no longer present for the select time period. Optionally, when the feedback signal is present, the microcontroller 221 may execute program instructions to appropriately handle the LOC condition such as, for example and without limitation, suspending alerting functionality temporarily until LOC condition resolves itself and/or sending an alert to an external device, a cell phone, a remote server, or the like, if the alert persists for a long time period. The alert may be communicated to the clinician and/or the patient. The alert may include one or more of audio, textual, and visual components.

The ICM 100 is further equipped with a communication modem (modulator/demodulator) 240 to enable wireless communication. In one implementation, the communication modem 240 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 240 may be implemented in hardware as part of the microcontroller 221, or as software/firmware instructions programmed into and executed by the microcontroller 221. Alternatively, the modem 240 may reside separately from the microcontroller as a standalone component. The modem 240 facilitates data retrieval from a remote monitoring network. The modem 240 enables timely and accurate data transfer directly from the patient to an electronic device utilized by a physician.

The ICM 100 includes sensing circuit 244 selectively coupled to one or more electrodes that perform sensing operations, through the switch 227 and the ETF circuit 229 to detect cardiac activity data indicative of cardiac activity. The sensing circuit 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 227 may be used to determine the sensing polarity of the cardiac signal by selectively closing the appropriate switches.

The output of the sensing circuit 244 is connected to the microcontroller 221 which, in turn, determines when to store the cardiac activity data of CA signals (digitized by the A/D data acquisition system 250) in the memory 260. For example, the microcontroller 221 may only store the cardiac activity data (from the A/D data acquisition system 250) in the memory 260 when a potential pause episode is detected and/or the electrodes are in an engaged state. The sensing circuit 244 receives a control signal 246 from the microcontroller 221 for purposes of controlling the gain, threshold, polarization charge removal circuitry (not shown), and the timing of any blocking circuitry (not shown) coupled to the inputs of the sensing circuit.

In the example of FIG. 2, a single sensing circuit 244 is illustrated. Optionally, the ICM 100 may include multiple sensing circuits, similar to sensing circuit 244, where the sensing circuits are coupled to two or more electrodes and controlled by the microcontroller 221 to sense electrical activity detected at the corresponding two or more electrodes. The sensing circuit 244 may operate in a unipolar sensing configuration or a bipolar sensing configuration. Optionally, the sensing circuit 244 may be removed entirely, and the microcontroller 221 perform the operations described herein based upon the CA signals and the LOC condition from the A/D data acquisition system 250 directly coupled to the electrodes.

The arrhythmia detector 234 of the microcontroller 221 includes an on-board R-R interval irregularity (ORI) process 236 that detects AF episodes using an automatic detection algorithm that monitors for irregular ventricular rhythms that are commonly known to occur during AF. For example, the ORI process 236 may implement the AF detection methods described in U.S. Pat. No. 8,135,456, titled "Device and Method for Detecting Atrial Fibrillation" the complete subject matter of which is incorporated herein by reference in its entirety.

The DAS 250 is coupled to one or more electrodes via the switch 227 to sample cardiac activity signals across any pair of desired electrodes. The data acquisition system 250 is configured to acquire cardiac electrogram (EGM) signals as CA signals, convert the analog data into digital data, and store the digital data as CA data for later processing and/or telemetric transmission to an external device 254 (e.g., a programmer, local transceiver, or a diagnostic system analyzer). The data acquisition system 250 is controlled by a control signal 256 from the microcontroller 221. The EGM signals may be utilized as the cardiac activity data that is analyzed for potential AF episodes.

By way of example, the external device 254 may represent a bedside monitor installed in a patient's home and utilized to communicate with the ICM 100 while the patient is at home, in bed or asleep. The external device 254 may be a programmer used in the clinic to interrogate the ICM 100, retrieve data and program detection criteria and other features. The external device 254 may be a handheld device (e.g., smartphone, tablet device, laptop computer, smartwatch and the like) that can be coupled over a network (e.g., the Internet) to a remote monitoring service, medical network and the like. The external device 254 facilitates access by physicians to patient data as well as permitting the physician to review real-time CA signals while collected by the ICM 100.

The ICM is further equipped with a memory 260. The microcontroller 221 is coupled to a memory 260 by a suitable data/address bus 262 and/or has the memory 260 integrated into the microcontroller 221 itself. The programmable operating parameters used by the microcontroller 221 are stored in memory 260 and used to customize the operation of the ICM 100 to suit the needs of a particular patient. Such operating parameters define, for example, detection rate thresholds, sensitivity, automatic features, activity sensing or other physiological sensors, and electrode polarity, etc.

The ICM 100 may also collect and utilize impedance data to monitor and determine the state of the one or more electrodes. The impedance measured may be expressed in terms of ohms. Alternatively, the impedance may be expressed as an admittance measurement. The admittance may be inversely related to the impedance. The impedance measured may vary based on the degree of electrode-tissue contact of the one or more electrodes. Therefore, change in impedance may be utilized to monitor and detect an LOC condition of the one or more electrodes corresponding to a disengaged state.

Figure 3:
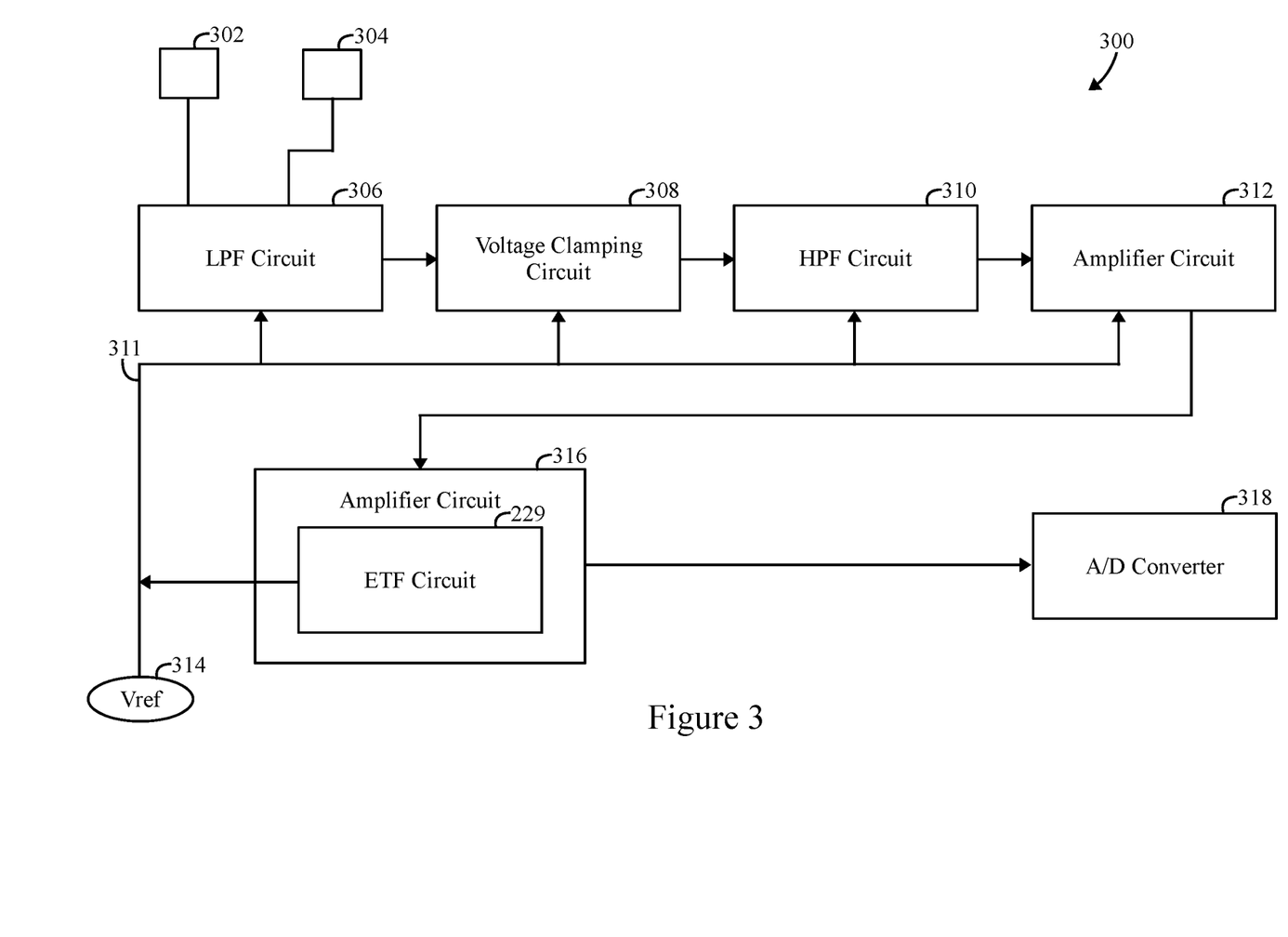
FIG. 3 illustrates a block diagram of one example of a circuit for detecting a loss of electrode-tissue contact (LOC) condition for an implantable cardiac monitor (ICM) in accordance with embodiments herein.

FIG. 3 illustrates a block diagram of one example of a circuit 300 for detecting an LOC condition for an ICM in accordance with embodiments herein. The circuit 300 includes electrodes 302, 304. In one example, electrode 304 is a case electrode. The electrodes 302, 304 are configured to sense analog CA signals when engaged with a tissue at a location remote from the heart. The electrodes 302, 304 exhibit an input impedance that varies based on the degree of electrode-tissue contact between the electrode surface area and the tissue (e.g., skin, subcutaneous skin, and the like). In the engaged state, the degree of electrode-tissue contact between the electrode surface area of the electrodes 302, 304 and the tissue maintains an input impedance at the one or more electrodes 302, 304 that is below a predetermined threshold value (e.g., 100 kΩ), which may be configured into the circuitry and/or programmed. In the disengaged state, the degree of electrode-tissue contact between the electrode surface area of the electrodes 302, 304 and the tissue results in an input impedance at the one or more electrodes 302, 304 that is above the predetermined threshold value.

The electrodes 302, 304 are connected to a low pass filter (LPF) circuit 306. CA signals sensed by the electrodes 302, 304 travel along a data signal path to the LPF circuit 306. The LPF circuit 306 attenuates the CA signals collected by the electrodes 302, 304 to reduce or remove frequencies higher than the selected cut-off frequency of the LPF circuit 306. The output of the LPF circuit 306 is provided as an input to a voltage clamping circuit 308. The voltage clamping circuit 308 provides protection for the circuit 300 from exposure to a defibrillation or other high voltage shock. The voltage clamping circuit 308 limits the incoming circuit voltage to a diode clamping voltage in either direction between the sense electrode 302 and the case electrode 304. The output of the voltage clamping circuit 308 is connected to the input of a high pass filter (HPF) circuit 310. The HPF circuit 310 attenuates CA signals collected by the electrodes 302, 304 with frequencies lower than the selected cut-off frequency of the HPF circuit 310 and removes offset introduced due to the gain of the first amplifier circuit 312. The HPF circuit 310 and LPF circuit 306 cooperate to establish the overall frequency response of the circuit 300. The LPF circuit 306 and the HPF circuit 310 output CA signals having a select frequency (e.g., higher than 0.5 and lower than 30 Hz) to exclude artifacts due to DC drift of the CA signals, high frequency signal fluctuations and the like.

The output of the HPF circuit 310 is connected to the input of a first amplifier circuit 312. The first amplifier circuit 312 is a differential amplifier having a select gain that accounts for most of the signal gain of analog CA signals processed by the circuit 300. The first amplifier circuit 312 may have a gain of, for example, 83.5. The output of the first amplifier circuit 312 is connected to a second amplifier circuit 316. The second amplifier circuit 316 has a select gain that is less than the gain of the first amplifier circuit 312. The second amplifier circuit has a gain of, for example, 3.8. The LPF circuit 306, the voltage clamping circuit 308, the HPF circuit 310, and the amplifier circuits 312, 316 are connected to, and generate outputs with respect to, a common voltage reference line 311. The voltage line 311 delivers a reference voltage (Vref) from a Vref source 314.

The second amplifier circuit 316 includes the ETF circuit 229. The ETF circuit 229 detects whether an LOC condition exists, corresponding to the disengaged state of one or more of the electrodes 302, 304, based on an input impedance at one or more of the electrodes 302, 304. In the engaged state, the degree of electrode-tissue contact between the electrode surface area of the electrodes 302, 304 and the tissue results in an input impedance at the one or more electrodes 302, 304 that falls below the predetermined threshold value (e.g., 100 kΩ) and the ETF circuit 229 does not generate any feedback signal component. In the disengaged state, the degree of electrode-tissue contact between the electrode surface area of the electrodes 302, 304 and the tissue results in an input impedance at the one or more electrodes 302, 304 that is above the predetermined threshold value (e.g., 100 kΩ). The ETF circuit 229 generates a feedback signal component in response to detection of an input impedance at the one or more electrodes 302, 304 exceeding a predetermined impedance threshold. The ETF circuit 229 generates the feedback signal component into the data signal path when the one or more electrodes 302, 304 exceeds the predetermined impedance threshold, indicating one or more of the electrodes 302, 304 is in the disengaged state.

The ETF circuit 229 interacts with at least the first amplifier circuit 312 to generates the feedback signal component into the data signal path. For example, the ETF circuit 229 superimposes the feedback signal component onto the voltage reference signal path such that the feedback signal component is superimposed onto the analog CA signals filtered and amplified by at least the circuits 306-312. The ETF circuit 229 generates the feedback signal component into the voltage reference signal path by modulating the Vref source 314 at a frequency that is distinguishable from CA signal components due to cardiac beats. The LPF circuit 306, the voltage clamping circuit 308, the HPF circuit 310, the first amplifier circuit 312, and the second amplifier circuit 316 are all referenced to the Vref source 314 and process signals sensed by the electrodes 302, 304 to form analog CA signals that include a physiologic characteristic of interest (COI). The physiologic COI includes various components of interest such as, for example and without limitation, components related to an R-wave and components related to a T-wave. R-waves and T-waves, corresponding to beats of a heart, occur at a rate of 60-120 beats per minute (cycles per minute) and frequencies of 1-2 Hz in the time domain. Even during a cardiac event (e.g., tachycardia), R-waves and T-waves occur with an RR interval and TT interval, respectively, in the time domain with frequencies of less than 5 Hz (e.g. less than 300 beats per minute). When the CA signals are considered in the frequency domain, an individual T-wave will generally comprise primary frequency components at frequencies of 5 Hz or less, whereas an individual R-wave will generally comprise primary signal components at frequencies less than 100 Hz. Accordingly, in the time domain, the physiologic COI are present in CA signals at frequencies of less than 5 Hz. In the frequency domain, the physiologic COI are present in CA signals at frequency components below the frequency of 100 Hz. In contrast, non-physiologic components of CA signals occur, in the time domain, at frequencies greater than 5 Hz. Non-physiologic components of CA signals occur, in the frequency domain, at frequencies greater than 100 Hz, thereby rendering non-physiologic components distinguishable from physiologic COI. By way of example, the feedback signal component oscillates at a first frequency (e.g., 104 Hz) within a first predetermined frequency range sensed by the electrodes 302, 304 in the analog CA signals. The ETF circuit 229 may be further configured to generate the feedback signal component at one or more of the first frequency, a first amplitude, and/or having a non-physiologic shape based on the input impedance at the electrodes 302, 304 exceeding the predetermined impedance threshold.

The output of the second amplifier circuit 316 is connected to an A/D converter 318. The A/D converter 318 converts the analog CA signals, including the feedback signal component, to digital CA signals by sampling the analog CA signals at a select rate. The A/D converter 318 also converts the feedback signal component, through downsampling, to an aliased second frequency (e.g., 26 Hz) within a second predetermined frequency range (e.g., higher than 8 and less than 30 Hz). The one or more processors of the ICM 100 identify a LOC condition when the feedback signal component is present within the digital CA signals at the aliased second frequency.

Figure 4:
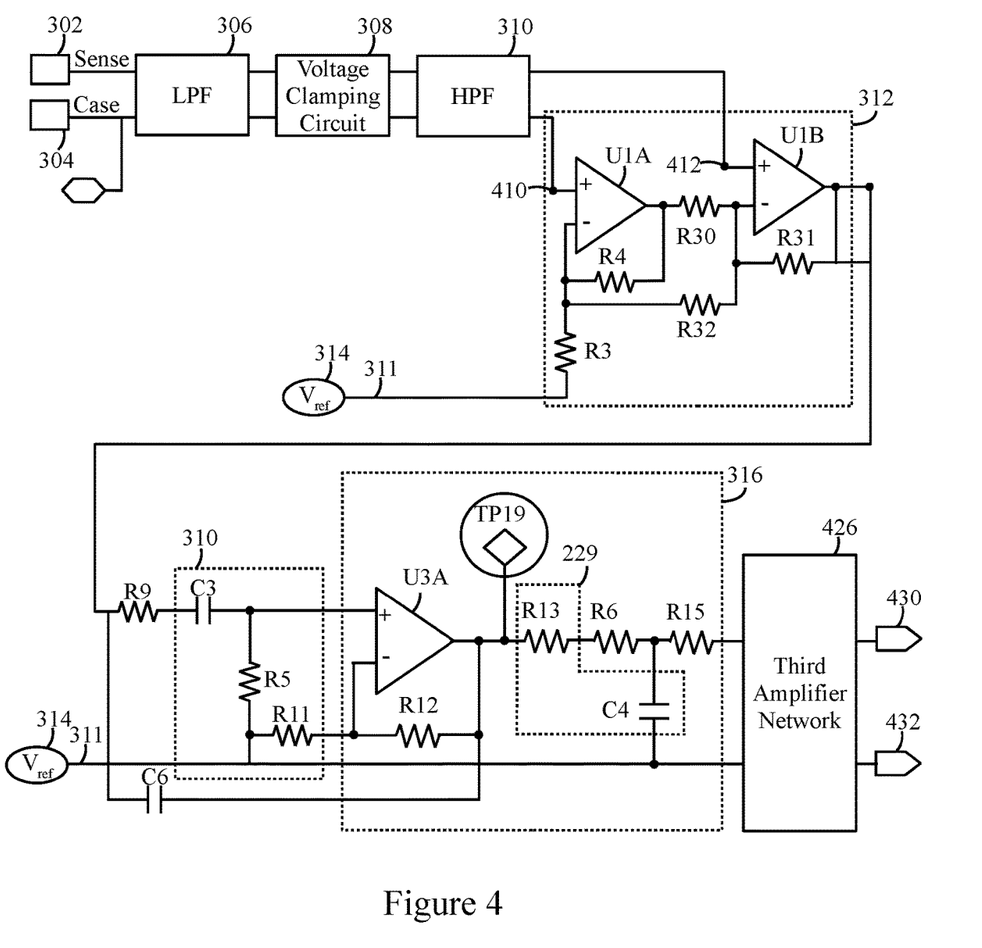
FIG. 4 illustrates a more detailed diagram of a first stage of an example circuit for detecting a LOC condition for an ICM in accordance with embodiments herein.

FIG. 4 illustrates a more detailed diagram of the example circuit of FIG. 3 in accordance with embodiments herein. The circuit 300 includes electrodes 302, 304. The electrodes 302, 304 sense analog CA signals when engaged with a tissue at a location remote from the heart. The electrodes 302, 304 exhibit an input impedance therebetween that varies based on the degree of electrode-tissue contact between the electrode surface area and the tissue (e.g., skin, subcutaneous skin, and the like). In the engaged state, the degree of electrode-tissue contact between the electrode surface area of the electrodes 302, 304 and the tissue maintains an input impedance that is below the predetermined threshold value (e.g., 100 kΩ). In the disengaged state, the degree of electrode-tissue contact between the electrode surface area of the electrodes 302, 304 and the tissue results in an input impedance that is above the predetermined threshold value.

The electrodes 302, 304 are connected to an LPF circuit 306. CA signals sensed by the electrodes 302, 304 travel along the data signal path to the LPF circuit 306. The LPF circuit 306 also includes additional LPFs described below. CA signals output by the LPF circuit 306 are provided as an input to the voltage clamping circuit 308.

The voltage clamping circuit 308 protects the circuit 300 upon exposure to a defibrillation or other high voltage shock. The voltage clamping circuit 308 clamps the circuit voltage to a diode clamping voltage in either direction between the sense electrode 302 and the case electrode 304. The CA signals output by the voltage camping circuit 308 are provided as an input to the HPF circuit 310.

The HPF circuit 310 and the LPF circuit 306 establish the frequency pass band of the circuit 300 (e.g., higher than 0.5 and lower than 30 Hz) and exclude artifacts due to DC drift of the CA signals and the like. The CA signals output by the HPF circuit 310 are provided as an input to the first amplifier circuit 312.

The first amplifier circuit 312 is formed by an operational amplifier (op amp) U1A connected in series to the negative terminal of an op amp U1B and the amplifier feedback resistors R3, R4, R30, R31, and R32 connected across the negative terminals of both U1A and U1B. The case line is connected at the node 410 to the positive input of the op amp U1A. The sense line is connected at the node 412 to the positive input of a second op amp U1B. The op amps U1A and U1B are further connected to, and generate outputs with respect to, the Vref source 314. The first amplifier circuit 312 may have a gain of, for example, 83.5. The output of U1B is connected in serial to resistor R9.

Resistor R9 isolates the capacitance output of op amp U1B to avoid capacitive loading of the second amplifier circuit 316. Resistor R9 is connected in serial to another HPF formed by capacitor C3 connected in series to resistor R5. In addition to forming part of the HPF circuit 310, capacitor C3 and resistor R9 combine to remove any offset to the signal originating from the first amplifier circuit 312.

The second amplifier circuit 316 is formed by op amp U3A connected, at the negative terminal thereof, in series to feedback gain resistors R11 and R12 and, at the output thereof, in series to the ETF circuit 229. The values of the feedback gain resistors R11 and R12 determine the gain of op amp U3A. The op amp U3A is further connected to, and generates output with respect to, the Vref source 314. Op amp U3A has a select gain that is less than the gain of the first amplifier circuit 312. The second amplifier circuit 316 has a gain of, for example, 3.8.

The ETF circuit 229 is an LPF formed by resistor R13 in series with capacitor C4. The ETF circuit 229 detects an LOC condition. For example, when the voltage at the node TP19 quickly crosses Vref the op amp U3A quickly switches from sinking to sourcing (or sourcing to sinking), causing an output current glitch that flows through capacitor C4. This adds a signal component to Vref which gets into the data signal path by feeding into op amps U1A, U2A, and U3A. This added signal component builds into the oscillation that represents the feedback signal component superimposed onto the CA signals. Alternatively, when the voltage at the node TP19 does not cross Vref, or crosses Vref slowly, the op amp U3A does not switch between sinking and sourcing, or does so slowly and smoothly, and the added signal component is not generated or superimposed onto the CA signals. The ETF circuit 229 may be configured to generate the feedback signal component at one or more of a first amplitude, a first frequency and/or having a non-physiologic shape based during an LOC condition due to an input impedance at the electrodes exceeding a predetermined impedance threshold.

In one embodiment, the ETF circuit 229 may be configured to generate a feedback signal component having a first frequency during an LOC condition. Resistor R13 and capacitor C4 control the frequency response of the feedback signal component by controlling the current in the voltage reference line 311 where capacitor C4 is attached. For example, while maintaining the functionality of the second amplifier circuit 316 as an LPF (e.g., a 32 Hz cut-off LPF), the oscillation frequency of the feedback signal component of the ETF circuit 229 may be configured by adjusting the values of resistor R13 and capacitor C4. For example, if the value of resistor R13 is increased and/or the value of capacitor C4 is increased, the frequency of the added signal component to Vref is decreased. Conversely, if the value of resistor R13 is decreased and/or the value of capacitor C4 decreased, the frequency of the added signal component to Vref is increased. The increase or decrease in the added signal component are related to, respectively, an increase or decrease in the oscillation frequency of the feedback signal component. The values of resistor R13 and capacitor C4 may be selected to be above any frequency exhibited by physiologic signals. The oscillation frequency of the feedback signal component may be configured to correspond to an aliased frequency dominantly at a select frequency (e.g., 26 Hz) within the second predetermined frequency range (e.g., higher than 8 and lower than 30 Hz) of the circuit.

In an additional or alternative embodiment, the ETF circuit 229 may be configured to generate a feedback signal component having a first amplitude based on an input impedance at the electrodes exceeding a predetermined impedance threshold. The amplitude of the feedback signal component of the ETF circuit 229 may be configured by adjusting the values of the amplifier feedback resistors R11, R12. Adjusting the values of the amplifier feedback resistors R11, R12 to increase (or magnify) the amplitude of the added signal component to Vref induced by sourcing of op amp U3B and, correspondingly, the amplitude of the feedback signal component. The values of resistors R11, R12 may be selected to increase the amplitude of the feedback signal component to be above any amplitude exhibited by physiologic signals. Additionally, the values of resistors R11, R12 may be selected to avoid saturating the op amp U3A with the input signal. CA signals corresponding to physiologic signal components are generally small and below the sensing threshold of the ICM 100. The amplitude of the feedback signal component may be increased such that the first amplitude is above the sensing threshold of the ICM 100. If the first amplitude of the feedback signal component is above the sensing threshold of the ICM 100, the one or more processors of the ICM 100 may detect the amplitude of the feedback signal component and, based thereon, declare an LOC condition based thereon. For example, the values of resistors R11, R12 are selected to increase the oscillation amplitude of the analog feedback signal component having a select frequency (e.g., at or near 102 Hz).

In an additional or alternative embodiment, the ETF circuit 229 may be configured to generate a feedback signal component having a non-physiologic shape during an LOC condition. The shape of the feedback signal component of the ETF circuit 229 may be configured to have a non-physiologic shape by adjusting the values of the resistors R12, R13. For example, the values of the amplifier feedback resistors R12, R13 may be selected to increase (or magnify) the amplitude of the added signal component to Vref to saturate the op amp U3B with the input signal. Op amp U3B produces the largest signal in the circuit. Saturating the op amp U3B with the input signal causes the op amp U3B to hit its dynamic range. When the op amp U3B hits its dynamic range, it produces a non-physiologic square wave during an LOC condition. The non-physiologic square wave produced during an LOC condition may be used as a unique signal signature to the one or more processors of the ICM 100 to identify and handle an LOC condition.

Figure 5A:
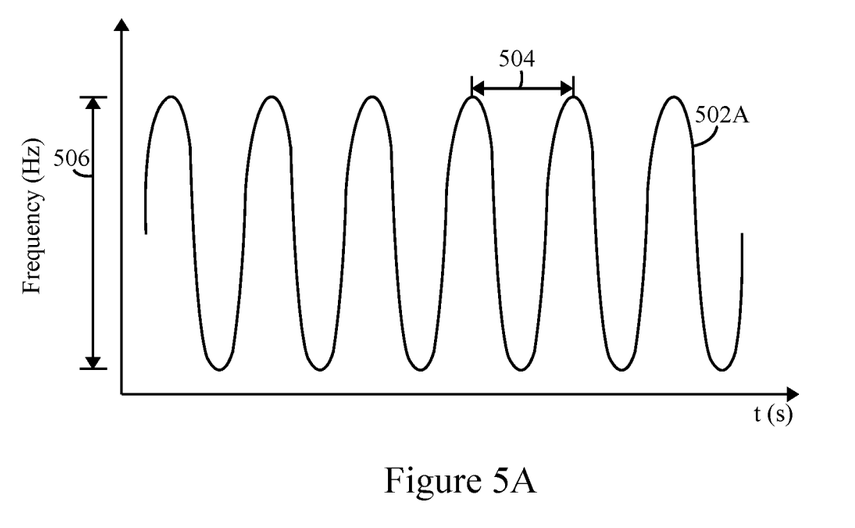
FIG. 5A illustrates an example of a feedback signal component in accordance with embodiments herein.

FIG. 5A is a illustrates an example of the feedback signal component 502A generated by the ETF circuit 229 during an LOC condition, when the one or more electrodes 302, 304 of the circuit 300 are in a disengaged state, in accordance with embodiments herein. (When the one or more electrodes 302, 304 of the circuit 300 are in an engaged state, the ETF circuit 229 does not generate the feedback signal component.) The feedback signal component 502A is a sinusoidal LOC signal characterized by a frequency 504 and an amplitude 506. The frequency 504 of the feedback signal component 502A generated by the ETF circuit 229 may be configured by adjusting the values of one or more of resistor R13 and capacitor C4. The frequency 504 of the feedback signal component 502A may be configured to correspond to an aliased frequency dominantly at a select frequency (e.g., 26 Hz) within the second predetermined frequency range (e.g., higher than 8 and lower than 30 Hz) of the circuit 300. Additionally or alternatively, the amplitude 506 of the feedback signal component 502A generated by the ETF circuit 229 may be configured by adjusting the values of the amplifier feedback resistors R11, R12. The amplitude 506 of the feedback signal component 502A may be increased (or magnified) such that the one or more processors of the ICM 100 detects the amplitude of the oscillating feedback signal component, without saturating the dynamic range of the op amp U3A, and can distinguish an LOC condition based thereon.

Figure 5B:
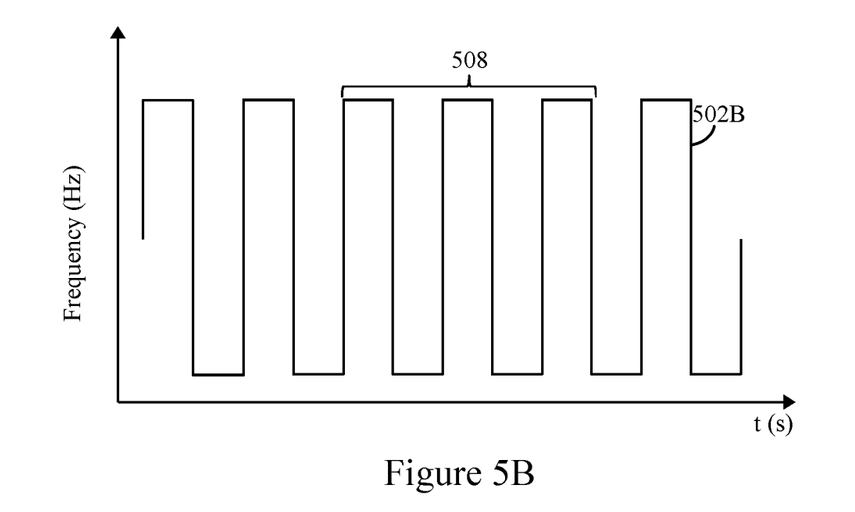
FIG. 5B illustrates another example of a feedback signal component in accordance with embodiments herein.

FIG. 5B illustrates another example of the feedback signal component 502B generated by the ETF circuit 229 during an LOC condition, when the one or more electrodes 302, 304 of the circuit 300 are in a disengaged state, in accordance with embodiments herein. The feedback signal component 502B is a sinusoidal LOC signal characterized by a non-physiologic shape 508. The non-physiologic shape 508 created by adjusting the values of one or more of resistors R12 and R13 to a large value such that the dynamic range of the op amp op amp U3A is saturated. Saturating the dynamic range of the op amp U3A generates a feedback signal component exhibiting the non-physiologic shape 508 (e.g., a square wave) during an LOC condition. This non-physiologic wave may be used as a unique signal signature by which the one or more processors of the ICM 100 can distinguish and properly handle LOC conditions.

The output of the second amplifier circuit 316 is fed into third amplifier network 426. The third amplifier network has a select gain (e.g., 2) and further filters the CA signals and feedback signal component. The circuit 300 has at least two output channels at the output side of the third amplifier network 426, channel IEGM 430 and channel RDET 432. Channel IEGM 430 has a select bandwidth (e.g., higher than 0.5 and lower than 30 Hz) and outputs the ECG signal seen by the physician. Channel RDET 432 has a select bandwidth (e.g., higher than 8 and lower than 30 Hz) and outputs the signal that is recorded by the one or more processors of the ICM 100 as well as used for R-wave detection. The third amplifier network 426 raises the frequency of the signal output at channel RDET 432 to a higher roll-on frequency (e.g., higher than 8 Hz). The value of the roll-on frequency for the channel RDET 432 is selected to ensure that no high amplitude T-waves are incorrectly sensed as R-waves. T-waves tend to have lower frequencies than R-waves and are attenuated by the additional filter. The channel IEGM 430 and the channel RDET 432 are fed to separate A/D converters. The channel IEGM 430 is sampled at a rate of 128 Hz, while the channel RDET 432 is sampled at a rate of 512 Hz. The channel RDET is sampled at a higher frequency to ensure low system latency to detect R-waves. Referring back to FIG. 3, the A/D converter 318 converts the feedback signal component received through channel RDET 432, through downsampling, to an aliased second frequency (e.g., 26 Hz) within a second predetermined frequency range (e.g., higher than 8 and lower than 30 Hz). The one or more processors of the ICM 100 identify an LOC condition when the feedback signal component is present within the digital CA signals at the aliased second frequency.

Methods for Detecting an LOC Condition

Figure 6:
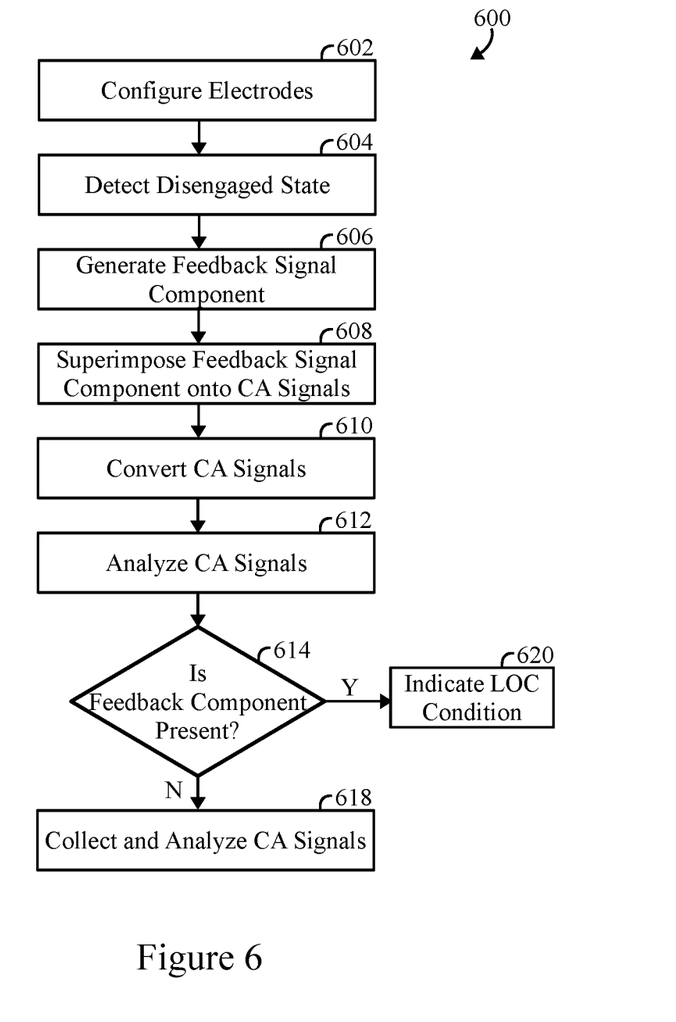
FIG. 6 illustrates a flow block diagram of a method for detecting a LOC condition for an ICM in accordance with embodiments herein.

FIG. 6 illustrates a computer-implemented method 600 for detecting an LOC condition for an ICM 100. In one example, the method 600 is performed utilizing the CA signals and feedback signal components detected and retrieved by the systems and methods described in detail in relation to FIGS. 1-5B. All or a portion of the operations of FIG. 6 may be implemented by one or more processors of the ICM 100 configured with executable instructions. It should be recognized that while the operations of method 600 are described in a somewhat serial manner, one or more of the operations of method 600 may be continuous and/or performed in parallel with one another. For example, the various operations of the ICM 100 may be continuous and/or performed in parallel with one another and/or other functions of the ICM 100. Also, unless otherwise indicated, each operation of method 600 is performed under the control of one or more processors configured with program instructions.

Beginning at 602, electrodes 302, 304 are configured to sense analog CA signals when engaged with tissue at a location remote from the heart. The one or more processors of the ICM 100 obtain CA signals at electrodes (e.g., one or more of electrodes 302, 304) during cardiac beats. The electrodes 302, 304 exhibit an input impedance that varies based on the degree of electrode-tissue contact between the electrode surface area and the tissue (e.g., skin, subcutaneous skin, and the like). The electrodes 302, 304 may transition between an engaged state and a disengaged state with respect to the tissue based on the degree of electrode-tissue contact. The disengaged state, corresponding to an LOC condition, may occur due to factors such as implantation technique, physician experience, patient postural changes, electrode surface area, subcutaneous tissue variation, and the like. In the engaged state, the degree of electrode-tissue contact between the electrode surface area of one or more of the electrodes 302, 304 and the tissue maintains an input impedance that is below a predetermined threshold value (e.g., 100 kΩ). In the disengaged state, the degree of electrode-tissue contact between the electrode surface area of the electrodes 302, 304 and the tissue results in an input impedance that is at or above the predetermined threshold value. CA signals sensed by the electrodes 302, 304 travel along a data signal path to the LPF circuit 306, the voltage clamping circuit 308, the HPF circuit 310, the first amplifier circuit 312, and to the second amplifier circuit 316.

At 604, the ETF circuit 229, implemented in the second amplifier circuit 316, detects when one or more electrodes 302, 304 are in the disengaged state. The ETF circuit 229 of the second amplifier circuit 316 includes resistor R13 connected in series to capacitor C4. The ETF circuit 229 detects an LOC condition corresponding to the disengaged state of one or more of the electrodes 302, 304 based on an input impedance exceeding the predetermined threshold value. For example, the ETF circuit 229 detects the LOC condition based on whether the value of the input impedance at one or more of the electrodes 302, 304 falls below or exceeds 100 kΩ. For example, when the voltage at the node TP19 exceeds Vref, the op amp U3A switches between sinking and sourcing. If the op amp U3A starts sourcing, excess current flows through capacitor C4 and into the voltage reference line 311 where capacitor C4 is attached. When excess current flows through capacitor C4, it disturbs Vref by adding a signal component to Vref into the data signal path due to the current now flowing onto the back side of op amp U3A.

At 606, the ETF circuit 229 generates a feedback signal component when the one or more electrodes 302, 304 are in the disengaged state. Generating includes the ETF circuit 229 generating the feedback signal component into the data signal path.

Generating may include generating the feedback signal component at a first amplitude based on an LOC condition. For example, the amplitude of the feedback signal component of the ETF circuit 229 may be configured by adjusting the values of the amplifier feedback resistors R11, R12. Adjusting the values of the amplifier feedback resistors R11, R12 to increase (or magnify) the amplitude of the added signal component to Vref induced by sourcing of op amp U3A and, correspondingly, the amplitude of the feedback signal component. The values of resistors R11, R12 may be selected to increase the amplitude of the feedback signal component to be above any amplitude exhibited by signals representing physiologic characteristics of interest, and above the sensing threshold of the ICM 100, but below a level that will saturate the op amp U3A.

Additionally or alternatively, may include generating the feedback signal component at a first frequency based on an LOC condition. The oscillation frequency of the feedback signal component of the ETF circuit 229 may be configured by adjusting the values of resistor R13 and capacitor C4 produce the feedback signal at the first frequency. For example, if the value of resistor R13 or capacitor C4 is increased, the frequency of the added signal component to Vref is reduced. Conversely, if the value of resistor R13 or capacitor C4 is decreased, the frequency of the added signal component to Vref is increased. Or if the value of resistor R13 is increased and the value of or capacitor C4 is decreased by a similar ratio, the frequency of the added signal component to Vref is unchanged, but other circuit behavior can be modified. Or if the value of resistor R13 is decreased and the value of or capacitor C4 is increased by a similar ratio, the frequency of the added signal component to Vref is unchanged, but other circuit behavior can be modified. The values of resistor R13 and capacitor C4 may be selected to generate the added signal component, and thus the feedback signal component, at a first frequency that is above physiologic signal frequencies. The frequency of the feedback signal component may be configured to correspond to the first frequency (e.g., 102 Hz) and/or the frequency corresponding to an aliased frequency (e.g., 26 Hz) within the second predetermined frequency range (e.g., higher than 8 and lower than 30 Hz) of the circuit.

Additionally or alternatively, generating may include generating the feedback signal component with a non-physiologic shape based on an LOC condition. For example, the values of the resistors R12, R13 may be selected to increase (or magnify) the amplitude of the added signal component to Vref to saturate the op amp U3B with the input signal. Saturating the op amp U3B with the input signal causes the op amp U3B to hit its dynamic range and produce a non-physiologic square wave during an LOC condition.

At 608, the ETF circuit 229 superimposes the feedback signal component onto the CA signals. The ETF circuit 229 interacts with at least the first amplifier circuit 312 to introduce the feedback signal component into the data signal path. For example, the added signal component feeds into op amps U1A, U1B of the first amplifier circuit 312 at the voltage reference line 311 of the Vref source 314. The feedback signal component oscillates at a frequency (e.g., 102 Hz) that is greater than frequencies associated with physiologic characteristics of interest (e.g., in the frequency domain, frequency components at or below 100 Hz).

At 610, the A/D converter 318 converts the analog CA signals to digital CA signals. The output of the second amplifier circuit 316 is connected in serial to an A/D converter 318. Converting further comprises converting the feedback signal, through downsampling, to an aliased second frequency within a second predetermined frequency range. For example, the A/D converter 318 converts the feedback signal component, through downsampling, to an aliased second frequency (e.g., 26 Hz) within a second predetermined frequency range (e.g., higher than 8 and lower than 30 Hz).

At 612, the one or more processors of the ICM 100 analyze the digital signals for a presence of the feedback signal component in connection with determining whether one or more of the one or more electrodes 302, 304 are in the engaged or disengaged state. The analyzing includes identifying an LOC condition when the feedback signal component having one or more of the first amplitude, the first frequency, and the non-physiologic shape is present within the digital CA signals. The one or more processors of the ICM 100 identify an LOC condition when the feedback signal component is present within the digital CA signals at the aliased second frequency.

At 614, the one or more processors of the ICM 100 determine if the feedback signal component is present in the digital CA signals. If the one or more processors of the ICM 100 determines that no feedback component is present in the digital CA signals, the process interprets the condition to indicate that the electrodes 302, 304 are in the engaged state. When the process interprets the condition to indicate that the electrodes 302, 304 are in the engaged state, flow moves to 618.

At 618, the one or more processors of the ICM 100 collect and analyze the CA signals to assess the presence or absence of a cardiac episode (e.g., a VT episode or the like). In one example, the arrhythmia detector 234 of FIG. 2 analyzes the CA signals to assess the rate of cardiac beats, the morphology of the QRS complexes, the duration of the QRS complexes, the AR intervals, T-wave morphology, and the like. Upon detection of a candidate arrhythmia episode, the arrhythmia detector 234 transmits a signal to the one or more processors indicating that a candidate arrhythmia episode (e.g., a candidate VT episode) is presented. Optionally, the one or more processors record an ensemble of cardiac beats and utilize a mathematical operation (e.g., averaging, mean, median, and the like) to combine the CA signals to form resultant CA signals that are analyzed for the candidate arrythmia.

Returning to 614, if the one or more processors of the ICM 100 determines that the feedback component is present in the digital CA signals, the process interprets the condition to indicate that the electrodes 302, 304 are in the disengaged state. When the process interprets the condition to indicate that the electrodes 302, 304 are in the disengaged state, flow moves to 620.

At 620, the one or more processors of the ICM 100 generate a signal indicating that the LOC condition exists and that one or more electrodes 302, 304 are in the disengaged state. Based on the signal indicating the LOC condition exists, the one or more processors of the ICM 100 can distinguish and execute program instructions to properly handle LOC conditions.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

When computer implemented methods are described herein, including through implementation with one or more processors, instructions for such one or more processors, may be received from the cloud storage environment. Additionally and alternatively, the computer implemented methods, including through implementation through one or more processors in one example includes implementation within the cloud environment and transmission of data packets from the cloud to an IMD or external device.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having second processor for execution of the code on the second device.

Aspects are described herein with reference to the figures, which illustrate example methods, devices and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable cardiac monitor (ICM), comprising:
electrodes configured to sense analog cardiac activity (CA) signals when engaged with tissue at a location remote from the heart, wherein one or more of the electrodes transition between an engaged state and disengaged state with respect to the tissue;
an analog to digital (A/D) converter communicating with the electrodes along a data signal path, the A/D converter configured to convert the analog CA signals to digital CA signals;
an electrode-tissue feedback (ETF) circuit provided along the data signal path between the electrodes and the A/D converter, the ETF circuit configured to generate a feedback signal component into the data signal path when one or more of the electrodes is in the disengaged state, the feedback signal component superimposed onto the analog CA signals; and
one or more processors configured to execute program instructions in connection with collecting and analyzing the digital CA signals when the one or more electrodes are in the engaged state.

2. The ICM of claim 1, further comprising an amplifier circuit connected to the electrodes along the data signal path and configured to amplify the analog CA signals, the ETF circuit interacting with the amplifier circuit to introduce the feedback signal component into the data signal path.

3. The ICM of claim 1, further comprising a voltage reference signal path configured to provide a reference voltage, the ETF circuit configured to generate the feedback signal component into the voltage reference signal path such that the feedback signal component is superimposed onto the analog CA signals.

4. The ICM of claim 1, wherein the ETF circuit is configured to detect a loss of electrode-tissue contact (LOC) condition corresponding to the disengaged state, and based thereon, the ETF circuit configured to introduce the feedback signal component.

5. The ICM of claim 4, wherein the ETF circuit is configured to detect the LOC condition based on an input impedance at the electrodes.

6. The ICM of claim 1, wherein the ETF circuit is configured to generate the feedback signal component in response to an input impedance at the electrodes exceeding a predetermined impedance threshold.

7. The ICM of claim 1, wherein the feedback signal component oscillates at a first frequency within a first predetermined frequency range that is greater than frequencies associated with physiologic characteristics of interest sensed by the electrodes in the analog CA signals.

8. The ICM of claim 7, wherein the A/D converter converts the feedback signal component, through downsampling, to an aliased second frequency within a second predetermined frequency range, the one or more processors identifying a loss of electrode-tissue contact (LOC) condition when the feedback signal component is present within the digital CA signals at the aliased second frequency.

9. The ICM of claim 1, wherein the ETF circuit is configured to generate the feedback signal component at a first amplitude based on an input impedance at the electrodes exceeding a predetermined impedance threshold, the one or more processors identifying a loss of electrode-tissue contact (LOC) condition when the feedback signal component having the first amplitude is present within the digital CA signals.

10. The ICM of claim 1, wherein the ETF circuit is configured to generate the feedback signal component at a first frequency based on an input impedance at the electrodes exceeding a predetermined impedance threshold, the one or more processors identifying a loss of electrode-tissue contact (LOC) condition when the feedback signal component having the first frequency is present within the digital CA signals.

11. The ICM of claim 1, wherein the ETF circuit is configured to generate the feedback signal component with a non-physiologic shape based on an input impedance at the electrodes exceeding a predetermined impedance threshold, the one or more processors identifying a loss of electrode-tissue contact (LOC) condition when the feedback signal component having the non-physiologic shape is present within the digital CA signals.

12. The ICM of claim 1, further comprising a housing enclosing the A/D converter, ETF circuit and one or more processors, the electrodes provided on the housing, the housing configured to be implanted in a subcutaneous pocket, the electrodes configured to engage within the subcutaneous pocket in connection with remotely monitoring heart activity.

13. A computer implemented method for detecting a loss of electrode-tissue contact (LOC) condition for an implantable cardiac monitor (ICM), the method comprising:
configuring electrodes to sense analog cardiac activity (CA) signals when engaged with tissue at a location remote from the heart, wherein one or more of the electrodes transition between an engaged state and disengaged state with respect to the tissue;

detecting when one or more of the electrodes is in the disengaged state;

generating a feedback signal component when the one or more of the electrodes is in the disengaged state;

superimposing the feedback signal component onto the analog CA signals; and converting the analog CA signals to digital CA signals, wherein the digital CA signals include the feedback signal component;

analyzing the digital CA signals for a presence of the feedback signal component in connection with determining whether one or more of the electrodes is in the engaged or disengaged state; and collecting and analyzing the digital CA signals when the one or more electrodes are in the engaged state.

14. The method of claim 13, further comprising:

amplifying the analog CA signals; and wherein the superimposing further comprises introducing a feedback signal component into the data signal path using an electrode-tissue feedback (ETF) circuit.

15. The method of claim 13, wherein the generating further comprises generating the feedback signal component into a voltage reference signal path such that the feedback signal component is superimposed onto the analog CA signals.

16. The method of claim 13, wherein detecting further comprises detecting the LOC condition based on an input impedance at the electrodes.

17. The method of claim 13, wherein converting further comprises converting the feedback signal, through downsampling, to an aliased second frequency within a second predetermined frequency range; and wherein analyzing further comprises identifying an LOC condition when the feedback signal component is present within the digital CA signals at the aliased second frequency.

18. The method of claim 13, wherein generating further comprises generating the feedback signal component at a first amplitude based on an input impedance at the electrodes exceeding a predetermined impedance threshold; and wherein the analyzing further comprises identifying an LOC condition when the feedback signal component having the first amplitude is present within the digital CA signals.

19. The method of claim 13, wherein generating further comprises generating the feedback signal component at a first frequency based on an input impedance at the electrodes exceeding a predetermined impedance threshold; and wherein the analyzing further comprises identifying an LOC condition when the feedback signal component having the first frequency is present within the digital CA signals.

20. The method of claim 13, wherein generating further comprises generating the feedback signal component with a non-physiologic shape based on an input impedance at the electrodes exceeding a predetermined impedance threshold; and wherein the analyzing further comprises identifying an LOC condition when the feedback signal component having the non-physiologic shape is present within the digital CA signals.

* * * * *